(12) United States Patent
Pedersen

(10) Patent No.: US 10,166,212 B2
(45) Date of Patent: Jan. 1, 2019

(54) ORAL USE OF ZINC AND COPPER GLUCONATES IN THE TREATMENT OF DIGITAL DERMATITIS

(71) Applicant: DANTRACE, Tårs (DK)

(72) Inventor: Jens Jorgen Pedersen, Tars (DK)

(73) Assignees: Dantrace-Danfeed IVS, Taars (DK); Distributors Processing, Inc., Porterville, CA (US)

( * ) Notice: Subject to any disclaimer, the term of this patent is extended or adjusted under 35 U.S.C. 154(b) by 0 days.

(21) Appl. No.: 15/736,957

(22) PCT Filed: Jun. 17, 2016

(86) PCT No.: PCT/DK2016/050201
§ 371 (c)(1),
(2) Date: Dec. 15, 2017

(87) PCT Pub. No.: WO2016/202346
PCT Pub. Date: Dec. 22, 2016

(65) Prior Publication Data
US 2018/0169056 A1 Jun. 21, 2018

(30) Foreign Application Priority Data
Jun. 17, 2015 (DK) .................. 2015 00345

(51) Int. Cl.
| | |
|---|---|
| *A61K 31/315* | (2006.01) |
| *A61K 31/30* | (2006.01) |
| *A23K 20/10* | (2016.01) |
| *A23K 20/20* | (2016.01) |
| *A23K 50/10* | (2016.01) |

(Continued)

(52) U.S. Cl.
CPC ............ *A61K 31/315* (2013.01); *A23K 20/10* (2016.05); *A23K 20/105* (2016.05); *A23K 20/30* (2016.05); *A23K 50/10* (2016.05); *A61K 31/30* (2013.01); *A61K 31/60* (2013.01); *A61K 33/30* (2013.01);

(Continued)

(58) Field of Classification Search
CPC ...... A23K 20/10; A23K 20/105; A23K 20/30; A23K 50/10; A61P 17/02
See application file for complete search history.

(56) References Cited

U.S. PATENT DOCUMENTS

| | | | | |
|---|---|---|---|---|
| 5,780,064 A | * | 7/1998 | Meisters ................ | A61K 33/40 424/616 |
| 2010/0233291 A1 | * | 9/2010 | Smithyman ............ | A01L 15/00 424/642 |
| 2014/0234386 A1 | * | 8/2014 | Hunter ................ | A01N 25/002 424/410 |

FOREIGN PATENT DOCUMENTS

| | | | | |
|---|---|---|---|---|
| WO | WO-9320749 A1 | * | 5/1998 | ............. A23K 40/00 |
| WO | WO-9820749 A1 | * | 5/1998 | ............. A23K 40/00 |

* cited by examiner

*Primary Examiner* — Savitha M Rao
(74) *Attorney, Agent, or Firm* — Trojan Law Offices

(57) ABSTRACT

There is disclosed a method of treating and preventing digital dermatitis in a herd of claw-bearing animals, in particular bovine digital dermatitis in a herd of cattle, comprising supplying zinc gluconate and copper gluconate to the feed of said herd in an amount between 35 to 500 mg zinc per kg dry feed per animal and between 5 and 40 mg copper per kg dry feed per animal and concomitantly treating any diagnosed digital dermatitis lesion in said herd of animals until the lesion is healed with a standard care topical treatment, in particular with a salicylic acid bandage topical treatment, continuing supplying zinc gluconate and copper gluconate to said herd and concomitantly treating any diagnosed lesion in said heard for at least 3 months, preferably for at least 6 months.

10 Claims, 5 Drawing Sheets

(51) Int. Cl.
    *A61K 45/06*         (2006.01)
    *A61K 31/60*         (2006.01)
    *A61K 33/30*         (2006.01)
    *A61K 33/34*         (2006.01)
    *A23K 20/105*       (2016.01)
    *A61P 17/02*         (2006.01)

(52) U.S. Cl.
    CPC .............. *A61K 33/34* (2013.01); *A61K 45/06* (2013.01); *A61P 17/02* (2018.01); *A61K 2300/00* (2013.01)

| Initial Data | Herd 1 | Herd 2 | Herd 3 | Herd 4 | Herd 5 | Herd 6 |
|---|---|---|---|---|---|---|
| Location | 1 | 1 | 1 | 1 | 2 | 3 |
| Race | Holstein-Friesian | Holstein-Friesian | Holstein-Friesian | Holstein-Friesian | Holstein-Friesian | Holstein-Friesian |
| Starting Date | 15.07.15 | 15.07.15 | 15.07.15 | 15.07.15 | 15.07.15 | 15.07.15 |
| Final Date | 16.03.16 | 16.03.16 | 16.03.16 | 16.03.16 | 16.03.16 | 16.03.16 |
| No. Cows | 409 | 370 | 154 | 200 | 189 | 401 |
| Fodder - Cows | Concentrates | Complete Diet | Complete Diet | Complete Diet | Complete Diet | Concentrates |
| Grazing | Yes | No | No | No | No | No |
| Feeding place | Milking carousel | Milking carousel | Robot | Robot | Robot | Robot |
| No. Heifers + Calves | 485 | 317 | 176 | 219 | 78 | 532 |
| Fodder - H + C | Complete Diet | Complete Diet | Complete Diet | Complete Diet | Complete Diet | Complete Diet |
| Grazing | Yes | No | No | No | No | No |
| Feeding place | Stall | Stall | Stall | Stall | Stall | Stall |
| Feed amount | 0.5 - 3.0 kg | 0.5 - 4.5 kg | 2.0 - 7.0 kg | 1.5 - 6.5 kg | 3.0 - 7.0 kg | 1.5 - 6.5 kg |
| Average feed | 2.5 kg | 3.0 kg | 4.0 kg | 4.6 kg | 4.5 kg | 4.5 kg |
| Claw cuttings per year (planned + acute) | 2 + acute | 3 + acute | 3 + acute | 2.5 + acute | 3 + acute | 4 + acute |
| Claw cutter | Owner | External 1 | Owner | External 2 | External 2 | External 3 |
| Reduced bandages | Yes | Yes | Yes | Yes | Yes | Yes |
| Reduce D.D. severity | Yes | Yes | Yes | Yes | Yes | Yes |
| Improved milk | Yes | Yes | Yes | Yes | Yes | Yes |
| Further effects observed | | Yes | | Yes | | Yes |

Fig. 5

ORAL USE OF ZINC AND COPPER GLUCONATES IN THE TREATMENT OF DIGITAL DERMATITIS

CROSS-REFERENCES TO RELATED APPLICATIONS

The present application is a U.S. National Stage Application under 35 U.S.C. 371 of PCT/DK2016/050201, filed on Jun. 17, 2016, which claims priority to Danish Patent Application PA 2015 00345, filed on Jun. 17, 2015.

FIELD

In the field of digital dermatitis in claw-bearing animals, and in particular in domesticated cattle, there is suggested use of zinc- and copper gluconates for oral use as easy uptake mineral sources in the treatment and prevention of digital dermatitis in claw-bearing animals, in particular in domesticated cattle.

BACKGROUND

Bovine Digital Dermatitis (BDD) is an infectious inflammation of the skin near the claws of cattle defined as a circumscribed superficial ulceration of the skin along the coronary band, commonly on the plantar, interdigital ridge of the rear foot. The disease is associated with substantial pain and discomfort to the animal affected.

Digital dermatitis (DD) in general is a condition affecting a broad range of domesticated animals belonging to the botanical order of artiodactyla or even-toed ungulates, such as sheep, goats, pigs and cattle. While the present disclosure focuses on domesticated cattle, it is considered that the methods of the invention with minor modifications (to adjust mineral amounts according to the biology of the animal) will have the same beneficial effects on other domesticated, even-toed ungulates in need of treatment against digital dermatitis.

It is common to refer to domesticated, even-toed ungulates as claw-bearing animals, in contrast to uneven-toed ungulates, such as horses, which are often called hoofed animals. In the present disclosure, the common term of claw-bearing animals is used, with the understanding that in this disclosure it refers to domesticated, even-toed ungulates, in particular to sheep, goats, pigs, and cattle, more particular to sheep, goats, and cattle, and most particular to cattle.

Digital dermatitis is a significant economic problem for the farming industry both in terms of costs of treatment, as well as in terms of lowered economic value of the animal. Digital dermatitis, in particular, is a significant problem in the dairy industry, as animals infested with digital dermatitis in general have significantly lower production rates of milk, and often co-associated with lowered milk quality, thereby posing a significant economic problem for the dairy farmers.

The most common sites of digital dermatitis lesions (Dörte Döpfer, CanWest Veterinary Conference, 2009) is the palmar/plantar interdigital ridge of the foot—especially on the rear feet, but other sites include the skin of the interdigital cleft, where lesions can be found on the interdigital hyperplasias, the skin around the dewclaws, the heel, sometimes underrunning the sole, and the dorsal aspect of the coronary band, where the lesions may be associated with a vertical wall crack.

A scoring system for the severeness of lesions in cattle infected with digital dermatitis is in general use, ranging from M0 (negative), M1 (early), M2 (acute), M3 (severe), to M4, severe and including late chronic lesions.

It is generally recognized (N. Capion, Sund Klov, 2014, N. Capion et al. Open J. Vet. Med. 2013, 3, 192-198) that digital dermatitis is caused by bacteria of the family *Treponema* spp. Up to 10 different bacterial phylotypes of this family having been identified in digital dermatitis lesions, but the mechanism of infection remains unknown. E.g. *Treponema* were found in all cell samples of infested skin in a Danish investigation (N. Capion, 2013) comprising 100 cell samples from dairy cattle in the Stratum Spinosum skin layer, along with numerous other bacteria associated with domesticated cattle, however *Treponema* was completely absent in cell samples from the same cattle in any other location except in the digital dermatitis lesions sampled, indicating the close association of *Treponema* with digital dermatitis.

Numerous treatments for digital dermatitis have been suggested, as well as improvements in stall hygiene and daily care of the cattle, in particular adequate claw chipping or cutting. Currently, no single treatment of digital dermatitis has proven adequate without concomitant improvements in stall hygiene and daily care of the cattle. In general, the bacteriological infection levels in stalls are significant under modern production requirements and medication is in general insufficient to maintain a complement free from digital dermatitis infections.

Medicinal efforts have focused primarily on vaccination, antibiotics, and topical treatment with e.g. salicylic acid, chlortetracycline HCL, or other agents with known antibacterial (and/or antifungal) effects upon topical application.

EP 2724724 A1 describes the use of sprayable copper and zinc chelate formulations for the treatment and prevention of epithelial infections in sheep, goats, horses, and cattle, wherein the compositions comprise micronized copper and zinc chelates suspended in a liquid, wherein the total amount of copper and zinc chelate ranges from 5 to 50 percent by weight, and less than 5% (w/v) of the chelates are dissolved. By topically applying the solutions to digital dermatitis lesions in cattle in three-day intervals, healing was achieved at each wound site (characterized M1 and M2) with two treatments as observed by inspection on day 10.

A particularly suitable form of topical treatment for digital dermatitis in claw-bearing animals, in particular in cattle, is the use of bandages comprising salicylic acid, in particular salicylic acid powder, topically applied to the digital dermatitis lesion site of the claw of the animal.

Schulz and Capion (The Veterinary J. Vol 198, Issue 2, November 2013, pages 518-523, "Efficacy of salicylic acid in the treatment of digital dermatitis in dairy cattle") report a study evaluating the efficacy of salicylic acid in the treatment of the digital dermatitis. A total of 201 DD lesions from 173 cows from four commercial dairy herds were evaluated at day 0 during routine hoof trimming and were allocated into two groups, namely, a control group given chlortetracycline spray, and a treatment group given 10 g of salicylic acid powder applied topically within a bandage. Pain, lesion size and clinical appearance (scored M0 to M4) were evaluated on days 3, 14 and 34 post-treatment. A change to M0 was defined as healing, while changes of M2 or M4 to M1 or M3 were classified as clinical improvements. Healing rates did not differ significantly between treatment groups at days 3 and 14. By day 34 the healing rate was fivefold better (P=0.01) for the treatment vs. the control group, with healing rates of 13.6% and 3.1%, respectively. By day 3, the rate of improvement was 2.5-fold better (P=0.02) for the controls. By day 34 the overall positive effect (i.e. healing and improvement) was 1.75-fold better (P=0.05) for the treatment group. Lesions from the control group were 2.2 times more likely (P=0.09) to have a pain score equal to 2 by day 14. The proportion of lesions getting smaller by days 14 and 34 was 2.5 times higher (P<0.08) for the treatment vs. the control group.

In the context of the present disclosure, salicylic acid bandages refer to any bandage for application to a digital dermatitis lesion site comprising sufficient salicylic acid, preferably as a powder, to effect a curing of the digital dermatitis lesion with an efficacy not worse than complete healing of the lesion in 30 days. Preferably, the amount of salicylic acid in the bandage shall be sufficient to achieve complete healing of the lesion in 20 days, more preferably in 15 days, even more preferably in 10 days, even more preferably in not more than 7 days, even more preferably in not more than 5 days, and most preferably in not more than 3 days. In the studies reported herein, bandages comprising sufficient salicylic acid powder to effect complete healing of a digital dermatitis lesion in a cow in usually two days were used in accordance with current Danish veterinary standards, with all lesions completely treated in 10 days or less.

It has been suggested that an improved clinical outcome can be achieved by supplying adequate amounts of trace minerals such as zinc or copper to cattle orally, e.g. in their diet as mineral supplements, e.g. Drendel et al. (The Pro. Anim. Sci, 21, p 217-224, 2005), Gomez et al. (J. Dairy Sci, 97, p 6211-6222), or N. Capion (Sund Klov, 2014). Concomitant treatment of digital dermatitis with topical antibacterial measures and zinc or copper mineral supplements have also been suggested.

Drendel et al. studied amino acid complexes of zinc, manganese and copper as a feed additive for dairy replacement heifers and the influence of these minerals in relation to claw disorders including digital dermatitis. The study was inconclusive regarding the overall effect of complex trace minerals on claw disorders. Gomez et al. studied the effect of trace minerals in a mineral premix comprising at least nine trace minerals, on the incidence of active digital dermatitis lesions in cattle and observed a statistically significant preventive effect of trace minerals on the prevention of digital dermatitis over a 45-day period.

With the present study, the inventor presents data indicating a beneficial effect on digital dermatitis in stabled cattle of orally supplying zinc and copper in the form of zinc and copper gluconates as feed additives for use in the prevention and cure of digital dermatitis. The tested procedure is applicable to the prevention and cure of digital dermatitis in all claw-bearing animals due to its simplicity and efficacy.

Zinc is a necessary component for the functioning of more than 300 different enzymes and plays a vital role in a large number of biological processes including skin healing and health. Zinc is a cofactor for the antioxidant enzyme, superoxide dismutase (SOD), and is involved in a number of enzymatic reactions in the carbohydrate and protein metabolism.

Zinc has a well-recognized importance as an immune-enhancing cofactor necessary for the regulation of T lymphocytes, CD4 cells, natural killer cells, and interleukin-2. In addition, it has been claimed that zinc possesses antiviral activity. Zinc is necessary for the maturation of sperm and normal fetal development. It is involved in sensory perception (taste, smell, and vision) and controls the release of stored vitamin A from the liver. In the endocrine system, zinc has been shown to regulate insulin activity and promote the conversion of the thyroid hormone thyroxine to triiodothyronine. It has been theorized that zinc improves claw integrity by speeding wound healing, increasing the rate of epithelial tissue repair and maintaining cellular integrity. Zinc is also required for the synthesis and maturation of keratin.

A particular problem with the administration of zinc to mammals is the low uptake of zinc in the digestive system. E.g., only 20% of added zinc is taken up by the digestive system when zinc is administered as pills of zinc oxide. The remaining zinc is excreted in the feces.

The present inventor has now surprisingly observed that feeding zinc, copper or, zinc and copper in the form of zinc gluconate and copper gluconate to stabled cattle already infected with digital dermatitis has a positive effect on the incidence level of digital dermatitis and on the general infectious level in the stabled cattle as measured as average cell count in milk.

SUMMARY OF THE INVENTION

The invention is disclosed in the present description and drawings and in the claims.

As detailed herein, there is disclosed zinc gluconate for oral use in the treatment of digital dermatitis in a claw-bearing animal.

As detailed further herein, there is disclosed copper gluconate for oral use in the treatment of digital dermatitis in a claw-bearing animal.

As detailed further herein, there is disclosed zinc gluconate and copper gluconate for oral use in the treatment of digital dermatitis in a claw-bearing animal.

As detailed further herein, there is disclosed zinc gluconate and/or copper gluconate for oral use in the treatment of bovine digital dermatitis, wherein the claw-bearing animal is a bovine.

As detailed further herein, there is disclosed zinc gluconate and/or copper gluconate for oral use in the treatment of digital dermatitis, wherein the domesticated claw-bearing animal is a sheep.

As detailed further herein, there is disclosed zinc gluconate and/or copper gluconate for oral use in the treatment of digital dermatitis, wherein zinc gluconate and/or copper gluconate is used as a feed additive.

As detailed further herein, there is disclosed zinc gluconate and/or copper gluconate for oral use in the treatment of digital dermatitis, wherein zinc gluconate and/or copper gluconate is mixed with silage.

As detailed further herein, there is disclosed zinc gluconate and/or copper gluconate for oral use in the treatment of digital dermatitis, wherein zinc gluconate and/or copper gluconate is mixed to a concentrates feed.

As detailed further herein, there is disclosed zinc gluconate and/or copper gluconate for oral use in the treatment of digital dermatitis, wherein zinc gluconate and/or copper gluconate are used concomitantly with a standard care topical treatment.

As detailed further herein, there is disclosed zinc gluconate and/or copper gluconate for oral use in the treatment of digital dermatitis, wherein the standard care topical treatment comprises a bandage with an antibacterial agent and/or an antifungal agent.

As detailed further herein, there is disclosed zinc gluconate and/or copper gluconate for oral use in the treatment of digital dermatitis, wherein the antibacterial agent and/or an antifungal agent is salicylic acid.

As detailed further herein, there is disclosed zinc gluconate and/or copper gluconate for oral use in the treatment of digital dermatitis, wherein the duration of the treatment is at least three weeks.

As detailed further herein, there is disclosed copper gluconate for oral use in the treatment of digital dermatitis, wherein the amount of copper in the feed is between 5 and 40 mg copper per kg dry feed.

As detailed further herein, there is disclosed copper gluconate for oral use in the treatment of bovine digital dermatitis, wherein the amount of copper in the feed is between 5 and 10 mg copper per kg dry feed.

As detailed further herein, there is disclosed zinc gluconate for oral use in the treatment of digital dermatitis, wherein the amount of zinc in the feed is between 35 to 500 mg zinc per kg dry feed.

As detailed further herein, there is disclosed zinc gluconate for oral use in the treatment of bovine digital dermatitis, wherein the amount of zinc in the feed is between 40 to 60 mg zinc per kg dry feed.

As detailed further herein, there is disclosed oral use of zinc gluconate for the manufacture of a medicament for the treatment of digital dermatitis in a claw-bearing animal.

As detailed further herein, there is disclosed oral use of copper gluconate for the manufacture of a medicament for the treatment of digital dermatitis in a claw-bearing animal.

As detailed further herein, there is disclosed oral use of zinc gluconate and copper gluconate for the manufacture of a medicament for the treatment of digital dermatitis in a claw-bearing animal.

As detailed further herein, there is disclosed oral use of zinc gluconate and copper gluconate for the manufacture of a medicament for the treatment of digital dermatitis in a claw-bearing animal, wherein the claw-bearing animal is a domesticated claw-bearing animal.

As detailed further herein, there is disclosed the use of salicylic acid bandages for the treatment of digital dermatitis in a claw-bearing animal concomitant with zinc gluconate and copper gluconate supplied to the diet of the claw-bearing animal.

As detailed further herein, there is disclosed a method of treating and preventing digital dermatitis in a claw-bearing animal, in particular bovine digital dermatitis in cattle, comprising supplying zinc gluconate and copper gluconate to the feed of the animal in an amount between 35 to 500 mg zinc per kg dry feed and between 5 and 40 mg copper per kg dry feed for a time period of at least 3 weeks, and concomitantly treating any diagnosed digital dermatitis lesion in the animal with a standard care topical treatment, in particular with a salicylic acid bandage, until the lesion is healed.

As further detailed herein, there is disclosed a method of treating and preventing digital dermatitis in a herd of claw-bearing animals, in particular bovine digital dermatitis in a herd of cattle, comprising supplying zinc gluconate and copper gluconate to the feed of the herd in an amount between 35 to 500 mg zinc per kg dry feed per animal and between 5 and 40 mg copper per kg dry feed per animal, and concomitantly treating any diagnosed digital dermatitis lesion in the herd of animals until the lesion is healed with a standard care topical treatment, in particular with a salicylic acid bandage topical treatment, continuing supplying zinc gluconate and copper gluconate to the herd, and concomitantly treating any diagnosed lesion in the herd for at least 3 months, preferably for at least 6 months.

As further detailed herein, there is disclosed the use of zinc gluconate and copper gluconate in a method of treating and preventing digital dermatitis in a claw bearing animal, in particular bovine digital dermatitis in cattle, the method comprising: supplying zinc gluconate and copper gluconate to the feed of the animal in an amount between 35 to 500 mg zinc per kg dry feed and between 5 and 40 mg copper per kg dry feed for a time period of at least 3 weeks, and concomitantly treating any diagnosed digital dermatitis lesion in the animal with a standard care topical treatment, in particular treating the lesion with a salicylic acid bandage, until the lesion is healed.

Use of zinc gluconate and copper gluconate in a method of treating and preventing digital dermatitis in a heard of claw bearing animals, in particular bovine digital dermatitis in a herd of cattle, the method comprising: supplying zinc gluconate and copper gluconate to the feed of the herd in an amount between 35 to 500 mg zinc per kg dry feed per animal and between 5 and 40 mg copper per kg dry feed per animal and concomitantly treating any diagnosed digital dermatitis lesion in the herd of animals until the lesion is healed with a standard care topical treatment, in particular with a salicylic acid bandage topical treatment, until the lesion is healed, in particular with a salicylic acid bandage topical treatment, followed by continuing supplying zinc gluconate and copper gluconate in the feed to the herd for at least 3 months, preferably for at least 6 months.

BRIEF DESCRIPTION OF THE DRAWINGS

FIG. 5 ("Table 1"): Table of the average feed supplied to particular herds.

DETAILED DESCRIPTION

Figure 1:
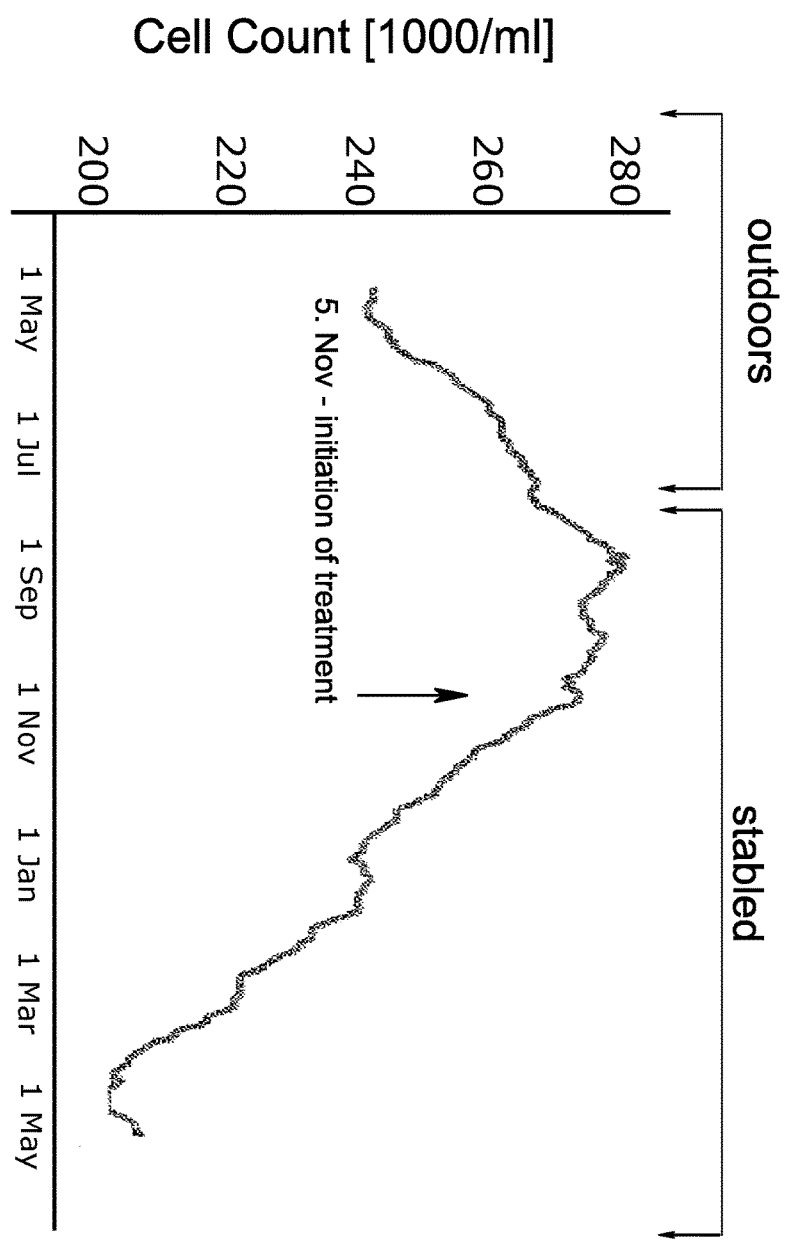
FIG. 1: Graph of cell count in milk vs. time for a stabled cowherd.

According to one of the embodiments of the present invention, zinc gluconate for oral use in the treatment of digital dermatitis in claw-bearing animals is disclosed herein, in particular zinc gluconate for oral use in the treatment of bovine digital dermatitis in domesticated cattle.

According to another embodiment of the present invention, copper gluconate for oral use in the treatment of digital dermatitis in claw-bearing animals is disclosed herein, in particular copper gluconate for oral use in the treatment of bovine digital dermatitis in domesticated cattle.

According to another embodiment of the present invention, zinc gluconate and copper gluconate for oral use in the treatment of digital dermatitis in claw-bearing animals is disclosed herein, in particular zinc gluconate and copper gluconate for oral use in the treatment of bovine digital dermatitis in domesticated cattle.

Zinc is important for growth and for the development and health of body tissues. Zinc gluconate is often used to treat zinc deficiency. It is recognized as a GRAS (generally recognized as safe) substance by the US Department of Health. The present inventor has surprisingly realized that zinc gluconate can be used to treat digital dermatitis in claw-bearing animals, in particular bovine digital dermatitis in domesticated cattle.

Copper is an essential trace element and copper deficiency is often treated with copper gluconate. Copper gluconate is recognized as a GRAS (generally recognized as safe) substance by the US Department of Health. The present inventor has surprisingly realized that copper gluconate can be used to treat digital dermatitis in claw-bearing animals, in particular bovine digital dermatitis in cattle.

Zinc gluconate and copper gluconate are safe dietary substitutes and the inventor surprisingly discovered that these substances have a therapeutic effect on already existing lesions as well as a stabilizing effect in preventing recurrence.

By treatment, we include both therapeutic and prophylactic treatment of an animal. In the context of the present disclosure, claw-bearing animals, in particular cattle, can be stabled, grazing and/or both stabled and grazing.

According to another embodiment of the present invention, zinc gluconate and copper gluconate for oral use in the treatment of digital dermatitis, wherein the claw-bearing animals are domesticated claw-bearing animals, is disclosed herein, in particular zinc gluconate and copper gluconate for oral use in the treatment of bovine digital dermatitis in domesticated cattle.

According to another embodiment of the present invention there is disclosed herein, zinc gluconate and copper gluconate for oral use in the treatment of bovine digital dermatitis, wherein the domesticated claw-bearing animals are domesticated cattle.

According to another embodiment of the present invention there is disclosed herein, zinc gluconate and/or copper gluconate for oral use in the treatment of bovine digital dermatitis in domesticated cattle, wherein the zinc gluconate and/or copper gluconate is used as a feed additive.

By themselves, zinc gluconate and copper gluconate can be supplied directly to an animal feed, or supplied in the form of a feed additive with further sources of minerals and vitamins. Preferably, zinc gluconate and copper gluconate are supplied as powders to the animal feed, in particular to concentrates or to silage.

According to another embodiment of the present invention there is disclosed herein, zinc gluconate and/or copper gluconate for oral use in the treatment of bovine digital dermatitis, wherein zinc gluconate and/or copper gluconate is mixed with silage.

According to another embodiment of the present invention there is disclosed herein, zinc gluconate and/or copper gluconate for oral use in the treatment of bovine digital dermatitis, wherein zinc gluconate and/or copper gluconate is mixed to a concentrates feed.

Other forms of oral delivery may be suitable without departing from the inventive concept described herein. Zinc gluconate and/or copper gluconate can for example, be mixed into the drinking water of the animals to be treated.

According to another embodiment of the present invention there is disclosed herein, zinc gluconate and/or copper gluconate for oral use in the treatment of bovine digital dermatitis, wherein the zinc gluconate and/or copper gluconate are used concomitantly with a standard care topical treatment.

According to another embodiment of the present invention there is disclosed herein, zinc gluconate and/or copper gluconate for oral use in the treatment of bovine digital dermatitis, wherein the standard care topical treatment is a bandage with an antibacterial agent and/or an antifungal agent.

An antibacterial and/or antifungal agent can be, but is not limited to, chlortetracycline HCL, oxytetracycline, or salicylic acid. In particular, salicylic acid is preferred as the antibacterial agent in the context of the present invention.

According to another embodiment of the present invention there is disclosed herein, zinc gluconate and/or copper gluconate for oral use in the treatment of bovine digital dermatitis, wherein the antibacterial agent is salicylic acid.

According to another embodiment of the present invention there is disclosed herein, zinc gluconate and/or copper gluconate for oral use in the treatment of bovine digital dermatitis, wherein the duration of the treatment is at least three weeks.

Since both zinc gluconate and copper gluconate are safe substances and the oral use of zinc gluconate and copper gluconate has been shown to have a preventive effect on the recurrence of digital dermatitis, the treatment duration is not limited to three weeks, rather it can, and preferably should, be longer. It is contemplated that the oral use of zinc gluconate and/or copper gluconate is continued for at least 1 month, at least 2 months, at least 3 months, at least 4 months, at least 6 months, at least 7 months, at least 8 months, at least 9 months, at least 10 months, at least 11 months, at least 12 months, at least 18 months, at least 24 months, at least 30 months or at least 36 months.

According to another embodiment of the present invention there is disclosed herein, copper gluconate for oral use in the treatment of digital dermatitis, in particular bovine digital dermatitis, wherein when copper gluconate is supplied to an animal feed, the amount of copper in the feed being between 5 and 40 mg copper per kg dry feed, more preferably between 5 and 35 mg copper per kg dry feed, more preferably between 5 and 30 mg copper per kg dry feed, more preferably between 5 and 25 mg copper per kg dry feed, more preferably between 5 and 20 mg copper per kg dry feed, more preferably between 5 and 15 mg copper per kg dry feed, more preferably between 5 and 10 mg copper per kg dry feed, more preferably between 6 and 9 mg copper per kg dry feed, more preferably between 7 and 9 mg copper per kg dry feed, more preferably 8 mg copper per kg dry feed.

According to another embodiment of the present invention there is disclosed herein, zinc gluconate for oral use in the treatment of digital dermatitis, in particular bovine digital dermatitis, wherein when zinc gluconate is supplied to an animal feed, the amount of zinc in the feed being between 35 to 500 mg zinc per kg dry feed, preferably between 35 to 450 mg zinc per kg dry feed, more preferably between 35 to 400 mg zinc per kg dry feed, more preferably between 35 to 350 mg zinc per kg dry feed, more preferably between 35 to 300 mg zinc per kg dry feed, more preferably between 35 to 250 mg zinc per kg dry feed, more preferably between 35 to 200 mg zinc per kg dry feed, more preferably between 35 to 150 mg zinc per kg dry feed, more preferably between 35 to 100 mg zinc per kg dry feed, more preferably between 35 to 90 mg zinc per kg dry feed, more preferably between 35 to 85 mg zinc per kg dry feed, more preferably between 35 to 80 mg zinc per kg dry feed, more preferably between 35 to 75 mg zinc per kg dry feed, more preferably between 35 to 70 mg zinc per kg dry feed, more preferably between 35 to 65 mg zinc per kg dry feed, more preferably between 40 to 60 mg zinc per kg dry feed, more preferably between 40 to 55 mg zinc per kg dry feed, more preferably between 40 to 50 mg zinc per kg dry feed, more preferably 45 mg zinc per kg dry feed.

Alternatively, and as discussed above, zinc and copper gluconates can be supplied to the feed as part of a feed additive comprising further mineral and vitamin supplements.

The manner in which modern industrial farming supplies feed to domesticated cattle permits the actual amount of zinc and copper eaten daily by any particular farm animal to vary quite significantly. E.g. in a milking carousel or with robot milking, cows will enter the milking facility at their own leisure to be relieved of the weight of the milk, which is simultaneously rewarded with free access to feed, inciting the individual cow to frequent the feeding and milking facility whenever it desires for optimal feeding and milking routines. However, such a voluntary feeding scheme restricts control with the actual daily uptake. Long-term uptake, however, is controllable and routinely implemented in the farming industry.

As such, the above limits on the amounts of zinc and copper gluconate present in the feed have proven efficient to obtain the benefits of the invention in modern dairy and cattle farming. Given the teaching provided in the present disclosure, the skilled person will be capable of adapting the present teaching to fixed feeding amounts, e.g. by using the information in Table 1 on the average feed supplied to a particular herd and cross-reference with the above information to obtain a daily average dosage suitable for use in the present invention.

According to another embodiment of the present invention there is disclosed herein, use of zinc gluconate for the manufacture of a medicament for the treatment of digital dermatitis, in particular bovine digital dermatitis, in claw-bearing animals.

According to another embodiment of the present invention there is disclosed herein, use of copper gluconate for the manufacture of a medicament for the treatment of digital dermatitis, in particular bovine digital dermatitis, in claw-bearing animals.

According to another embodiment of the present invention there is disclosed herein, use of zinc gluconate and copper gluconate for the manufacture of a medicament for the treatment of digital dermatitis, in particular bovine digital dermatitis, in claw-bearing animals.

According to another embodiment of the present invention there is disclosed herein, use of zinc gluconate and copper gluconate for the manufacture of a medicament for the treatment of digital dermatitis, in particular bovine digital dermatitis, wherein the claw-bearing animals are domesticated claw-bearing animals, in particular domesticated cattle.

As detailed further there is disclosed a method of treating and preventing digital dermatitis in a claw-bearing animal, in particular bovine digital dermatitis in cattle, comprising supplying zinc gluconate and copper gluconate to an animal feed in an amount between 35 to 500 mg zinc per kg dry feed and between 5 and 40 mg copper per kg dry feed for a time period of at least 3 weeks, and concomitantly treating any diagnosed digital dermatitis lesion in the animal with a standard care topical treatment, in particular with a salicylic acid bandage, until the lesion is healed.

As further detailed herein, there is disclosed a method of treating and preventing digital dermatitis in a herd of claw-bearing animals, in particular bovine digital dermatitis in a herd of cattle, comprising supplying zinc gluconate and copper gluconate to the feed of the herd in an amount between 35 to 500 mg zinc per kg dry feed per animal and between 5 and 40 mg copper per kg dry feed per animal, and concomitantly treating any diagnosed digital dermatitis lesion in the herd of animals with a standard care topical treatment until the lesion is healed, in particular with a salicylic acid bandage topical treatment, continuing supplying zinc gluconate and copper gluconate to the herd and concomitantly treating any diagnosed lesion in the herd for at least 3 months, preferably for at least 6 months.

Generally, it is known to treat digital dermatitis concomitantly with adjusted mineral feed and standard topical care. The present invention demonstrates for the first time that a synergistic effect exists between lesion treatment on a short time scale (days) by the topical treatment and a prevention effect over a longer time scale (months), which is mediated by zinc gluconate and copper gluconate, alone or in combination. This synergistic effect, which the present inventor has now realized exist when using zinc- and copper gluconates with topical treatment, in particular salicylic acid bandages, is completely unexpected and not foreseen by the prior art. Concomitant treatments, as known from the prior art, have only succeed in healing lesions temporarily, but not in obtaining significant preventive effects. The present inventor speculates, but does not consider himself bound by any particular theory, that gluconates of zinc and copper are particularly well suited for absorption into the body from the feed by claw-bearing animals over other known mineral complexes of zinc and copper known to be used in animal feed for claw-bearing animals, and in particular to be known for use with cattle.

EXAMPLES

The invention is further demonstrated by way of non-limiting examples.

Example 1

As exemplified herein, the feasibility of the inventive concept was evaluated in a pilot project in two stabled cowherds, comprising one herd of lactating dairy cows, and one herd of heifers, both herds stabled in separate cowsheds at the same farm in the Northern Jutland region of Denmark.

Prior to the test phase, both herds were observed with widespread digital dermatitis. Both herds were fully supplied with zinc, in the form of zinc oxide, and copper, in the form of copper sulfate, according to the current guidelines (NorFor 2013—Nordic Feed Evaluation System).

For ethical reasons, all animals diagnosed with digital dermatitis lesions were treated efficiently and to completion with salicylic acid bandages against the lesions. The pilot test therefore comprised concomitant treatment of diagnosed digital dermatitis lesions with salicylic acid bandages at the lesion site, together with changed feed concentrates, i.e. from concentrates comprising zinc oxide and copper sulfate to concentrates comprising zinc gluconate and copper gluconate.

Treatment with salicylic acid bandages is a rapid treatment for digital dermatitis lesions with a time to complete healing of the lesion of less than a week. Typically, bandages are worn by the cattle on the lesion site for two days, which in most cases is sufficient for efficient and complete healing of the lesion.

Dairy Cows:

A first test group consisted of a dairy cattle herd of 370 individuals. The herd had significant problems with bovine digital dermatitis lesions prior to the pilot project, and on the average 43.6 lesions per month were treated with salicylic acid bandages (with recurring lesions in all herd members) as measured over a 32 month period, including cows with multiple lesions. In total, about 24% of all herd members would be in treatment at any point during the 32 months preceding the present pilot project. This total is consistent with the overall digital dermatitis lesion prevalence for Denmark, reported at about 21% (Capion, 2013).

The herd was fully supplied with zinc and copper according to the current NorFor norm (Håndbog i Kvæghold, 2013) prior to initiation of the pilot project, in the form of 8 mg copper per kg dry feed, supplied as copper sulfate, and 45 mg zinc per kg dry feed, supplied as zinc oxide. Minerals were added to the concentrates feed and supplied to the cows after milking. The total supply of concentrates to a cow was from 2 kg to 10 kg of cake per day.

In the pilot project, zinc and copper were supplied in the same amounts, but now in the form of gluconates. No changes in total amount of zinc and copper were permitted.

The herd was stabled for the entire pilot project period. During the project period, the overall health of the claws was assessed concomitantly with claw cutting, which was performed as necessary, cf. FIG. 2.

The pilot project initiated on Nov. 5, 2014 and the herd was monitored until May 7, 2015. Claw cutting was undertaken on Feb. 26, 2015, Apr. 15, 2015, and May 7, 2015, yielding a total project time of approximately 6 months. The project was terminated when the herd was released from the cowshed to outdoors grazing. The period of outdoors grazing for the observed herd is from around May 1 to around Sep. 1.

The time between individual claw cuttings was significantly longer than the necessary healing time for digital dermatitis lesions using salicylic acid bandages such that no cow would be counted twice for the same bandage. Consequently, any observed further lesion is the result of a new infection rather than the continuation of an existing.

The total cell count in the milk produced in the herd was followed during a one-year period; 6 months prior to the project and during the 6 months of the pilot project, cf. FIG. 1. Total cell count is used in the dairy industry as a rough measure of milk quality and as a diagnostic tool for e.g. mastitis. The lower the total cell counts, the higher the economic value of the milk. The total cell count was followed from May 1, 2014 to May 14, 2015, i.e. one week past the termination of the pilot project, corresponding to the first week of outdoors grazing in 2015.

Results:

FIG. 1 details the average of the total cell count in the milk produced by the herd in units of 1000 cells/ml. During the observation period, the heard went from around 240 k cells/ml up to around 280 k cells/ml before the change of diet, and down to around 200 k cells/ml at its lowest point after the change of diet. After release to outdoors grazing at the end of the pilot project, the cell count appears to remain at the lower level of around 200 k cells/ml, indicative of a potential persisting preventive effect of the continued treatment with zinc gluconate and copper gluconate against bacterial infections, in particular against *Treponema* spp.

During the first observation period, corresponding to the outdoors grazing period of 2014, total cell counts in the produced milk increased continuously, in an approximately linear manner with time, from around 240 k cells/ml and up to around 280 k cells/ml. This effect is common to grazing milk cows irrespective of the number of digital dermatitis lesions in a herd.

To eliminate the effect on the milk quality from outdoors grazing in the project results, a two months stabilizing initial period was observed prior to initiation of the pilot project. During this period, from about September 1 to Nov. 1, 2014, the total cell count remained at a high value of around 280 k cells/ml, decreasing slightly from a maximum of around 280 k cells/ml at the end of the grazing season to around 275 k cells/ml at project start. This decrease is within the scatter between individuals in the herd and is not considered significant.

During the project period, the average total cell count for the herd decreased from around 275k cells/ml to around 200 k cells/ml. The decrease appears linear with time. In economic terms this corresponds to 1% extra earnings from improved milk quality at current (2015) rates for a herd of the size of the observed.

Figure 2:
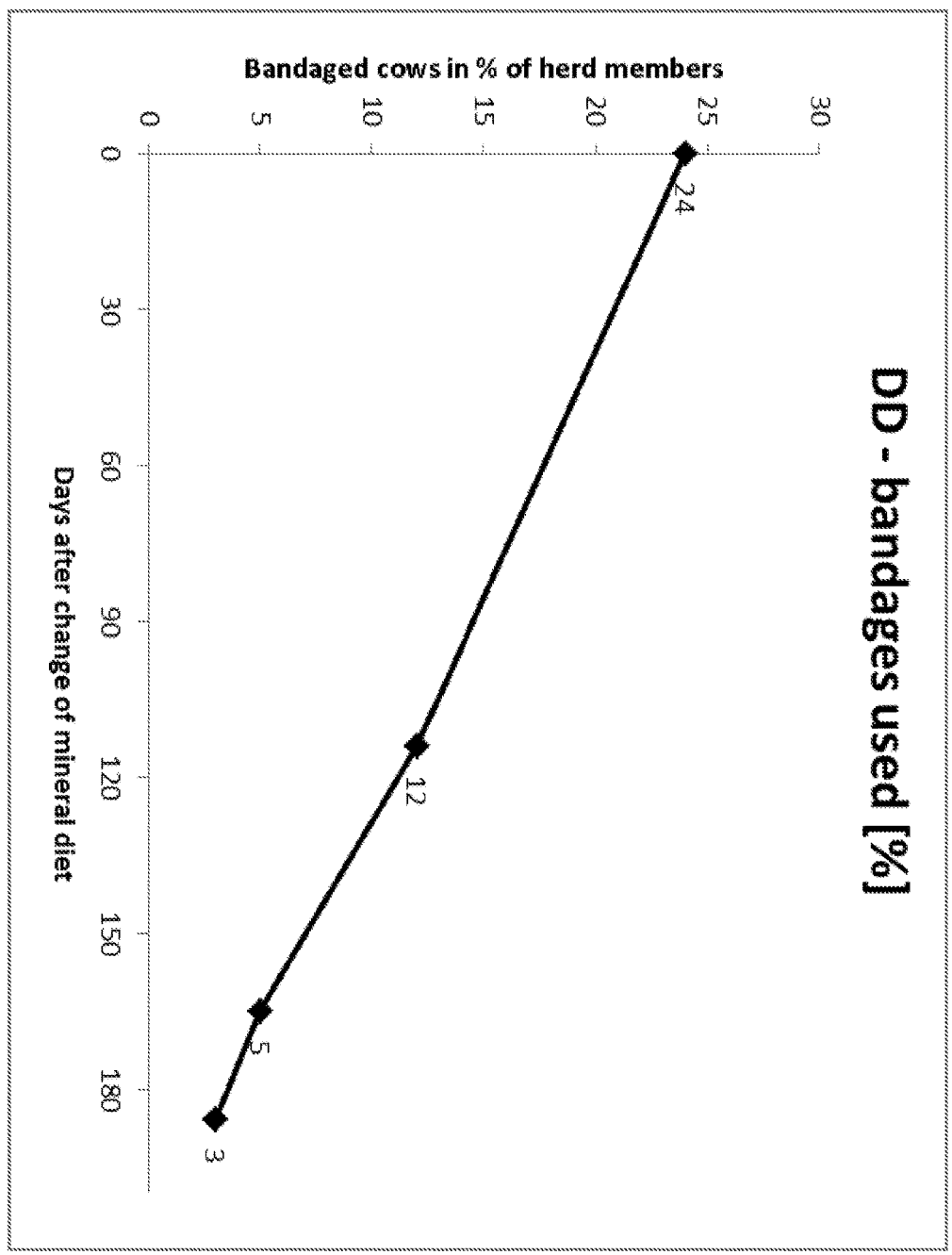
FIG. 2: Graph of healing progression vs. time for a stabled cowherd.

FIG. 2 details the number of salicylic acid bandaged cows in percent of herd members. As detailed above, same-cow multiple digital dermatitis lesions were initially common in the herd. During the project period, same-cow multiple digital dermatitis lesions were no longer observed after healing of the initial lesions using the bandages.

The number of recurring lesions went down significantly as well. At the claw cutting of Apr. 17, 2015 only few cows not in treatment were observed with preliminary indications of digital dermatitis lesions, and at the termination of the project, no cows not in treatment were observed to have preliminary indications of digital dermatitis lesions.

Heifers:

A second test group consisted of a herd of 420 heifers raised for sale. While the total herd size was relatively constant, individuals would enter and leave the herd as commercially required. For this reason, the results presented for this herd are of an indicative nature only.

The herd had significant problems with digital dermatitis lesions prior to the pilot project, at a digital dermatitis lesion prevalence consistent with the overall digital dermatitis lesion prevalence for Denmark, reported at about 21% (Capion, 2013).

The herd was fully supplied with zinc and copper according to the current NorFor norm (Hàndbog i Kvæhold, 2013) prior to initiation of the pilot project, in the form of 8 mg copper per kg dry feed, supplied as copper sulfate, and 45 mg zinc per kg dry feed, supplied as zinc oxide. Minerals were added to the feed in the form of silage (mixed in), and supplied to the heifers according to the established feeding scheme at the farm. A heifer is eating from 20 to 30 kg of silage per day and hence minerals supplied with silage are more diluted than when supplied in the form of concentrates, i.e. as compared to the lactating cows, which were supplied from 2 kg to 10 kg of cake per day.

In the pilot project, zinc and copper were supplied in the same amounts as before enrollment into the study, but now in the form of gluconates. No changes in total amount of zinc and copper were permitted from the original feeding scheme.

The herd was stabled for the entire pilot project period. During the project period, the overall health of the claws was assessed concomitantly with claw cutting, which was performed as necessary.

Results:

It was observed that in the herd, digital dermatitis lesions would disappear following the concomitant treatment of the lesions with salicylic acid bandages and the changed mineral diet over the six months period of observation, in correspondence with the observations on the dairy herd detailed above.

A slight delay of 3-4 weeks before onset of the beneficial effect of the concomitant treatment compared to the results for the lactating cows was observed, as will be discussed below.

Overall, however, concomitant treatment of digital dermatitis lesions in heifers with zinc- and copper gluconates together with salicylic acid bandages was as efficient for heifers as for lactating cows in curing digital dermatitis and preventing recurrence.

Example 2

The feasibility of the inventive concept was further evaluated in six cowherds, one herd both stabled and grazing and five herds fully stabled; each cowherd comprising: cows, heifers, and calves; in a cross-herd observation study. All six herds were stabled on different farms in three different locations across two regions of Denmark. Herd number 1 corresponds in part to the herds for which results were reported in Example 1, but now expanded to the entire complement of cattle on the farm. All cattle were of the race Holstein-Friesian (HF), in order to eliminate cross-racial effects from the data. The period of observation was 7 months.

The herds were enrolled into the study "as are", in the sense that the only change to the daily operation of the farm and the feed received by the cattle would be the change of the mineral sources, from zinc oxide and copper sulfate to zinc gluconate and copper gluconate. No further changes were accepted.

The herds were fully supplied with zinc and copper according to the current NorFor norm (Håndbog i Kvæghold, 2013) prior to initiation of the observation period. Only herd 1 was allowed outdoors grazing during the observation period. All herds had significant problems with bovine digital dermatitis lesions prior to the observation period. The total number of digital dermatitis lesions in the herds being consistent with the overall digital dermatitis lesion prevalence for Denmark, reported at about 21% (Capion, 2013). For Herd 1, only heifers and calves were new to the study. The cows treated and reported in Example 1 remained at a very low recurrence level of digital dermatitis (compare FIG. 2).

All animals diagnosed with digital dermatitis lesions were treated efficiently and to completion with salicylic acid bandages against the lesions. The cross-herd observation experiment therefore comprised concomitant treatment of diagnosed digital dermatitis lesions with salicylic acid bandages at the lesion site, together with changed feed from concentrates of zinc oxide and copper sulfate to feed comprising zinc gluconate and copper gluconate.

Across the board, it was observed in all herds that the number of applied salicylic acid bandages necessitated by digital dermatitis lesions in the cattle went down, as did the severity of the observed digital dermatitis lesions as measured on the M0-M4-scale. Likewise, across the board, it was observed that the total cell count in produced milk went down in the observed milk herds.

Surprisingly, but explainable, the number of applied bandages went down the most in those herds where claw cutting was performed by the herd owner him/herself. A follow-up check with the external claw cutters identified an unreported treatment practice applied by the external claw cutters, who would routinely apply bandages to digital dermatitis lesion sites where, although the lesion would have been healed, scar tissue had formed over the lesion, thereby treating the former lesion site unnecessarily. Contrary to this, in both herds where the owners were active as claw cutters themselves, the decision to continue or cease salicylic acid bandage treatment was made by palpating the healed, but scarred lesion site, and if no pain-reaction in the cow was observed, ceasing salicylic acid bandage treatment at this site. Overall-reported herd infestation level was observed at about 3-5% in the owner cut herds (consistent with the results of FIG. 2) and at about 10% in externally claw-cut herds at the end of the 7 months observation period.

For the cattle of Herd 6, a delay period of 3-4 weeks was observed, before a beneficial effect could be observed of the concomitant treatment with salicylic acid bandages and zinc and copper gluconates in the feed, in parallel with the observation made for the herd of heifers of Example 1. A unifying factor for the heifer herd of Example 1 and for the cattle herds of Herd 6 was that as well the heifers of Example 1 as the cattle of Herd 6 had received topical treatment (footbath) with copper sulfates preventive against digital dermatitis before being enrolled in the studies. It appears therefore, that such copper sulfates footbath treatment may inhibit the efficacy of the salicylic acid bandage lesion treatment, until the trace level of copper sulfate in the skin around the claws has become sufficiently reduced.

Figure 3:
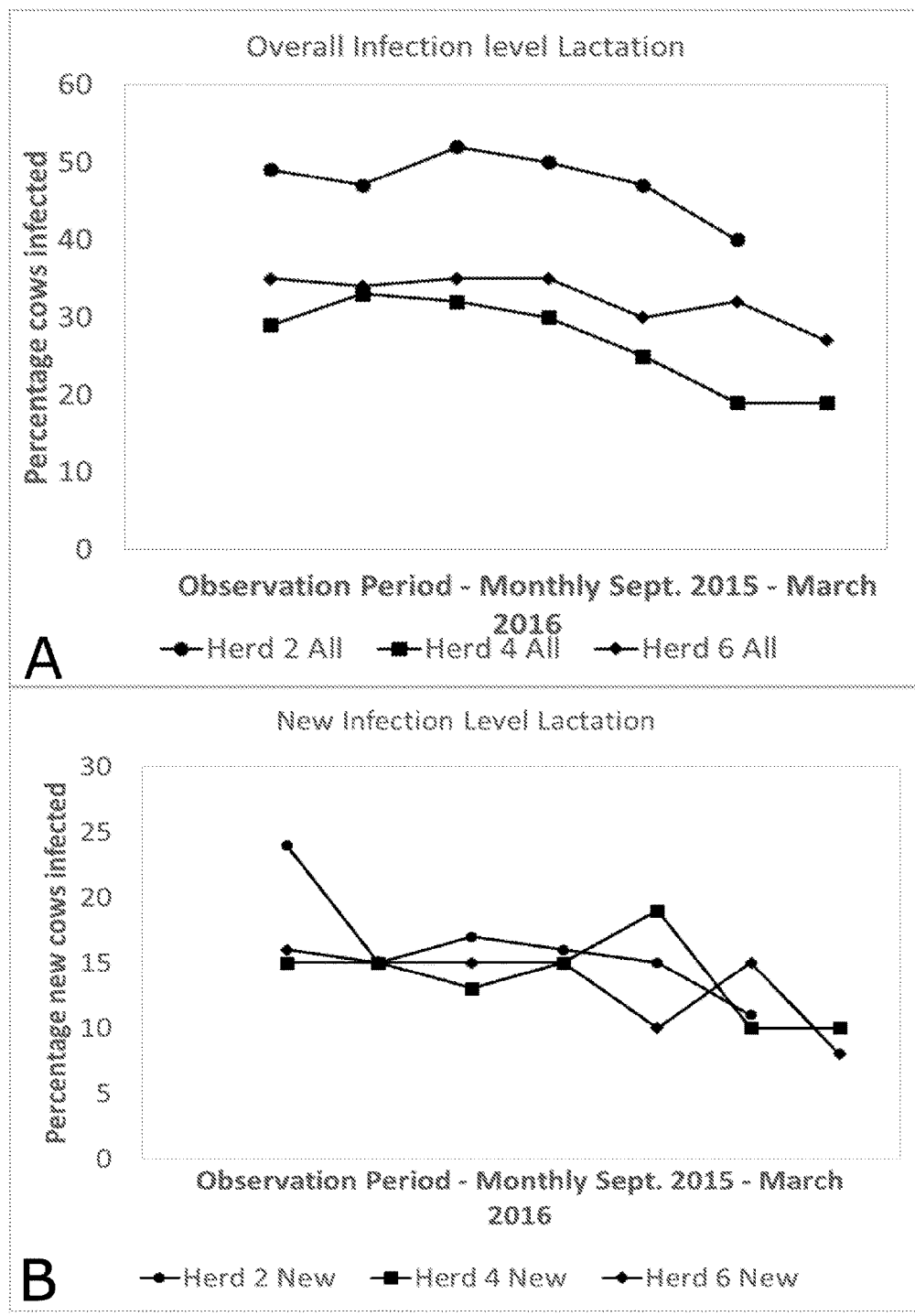
FIG. 3: Infection level in lactating cows.

FIG. 3A details the effect of the changed mineral diet on the overall bacterial infection level in lactating cows observed with a bacterial infection at yield control in three of the five herds, which were not grazing (Herds 2, 4, 6). No data was available for Herds 3 and 5. Also shown (FIG. 3B) is the level of bacterial new-infestation in lactating cows, which were observed as bacterially uninfected at the previous yield control. In accordance with good agricultural practice and animal ethical standards, cows observed with a bacterial infection receive treatment against the infection. This practice was observed also in the present study.

It can be observed (FIG. 3A) that overall levels of infections are high in the herds (above at least 30%) and fairly constant between September 2015 and Dec. 2015, at which point the overall infection level starts to decrease in all the complements observed (971 cows total). The same phenomena are apparent in the data of FIG. 3B. This observation is consistent with a bacterial origin of digital dermatitis, wherein the bacterial origin is concomitantly treated with salicylic acid bandages, and the changed diet to zinc and copper gluconate in the feed, such that when the bacterial origin of digital dermatitis is treated and prevented, this source of bacteria is reduced. Thus cows presenting with bacterial infections due to digital dermatitis no longer contribute to the overall complement infection level.

Figure 4:
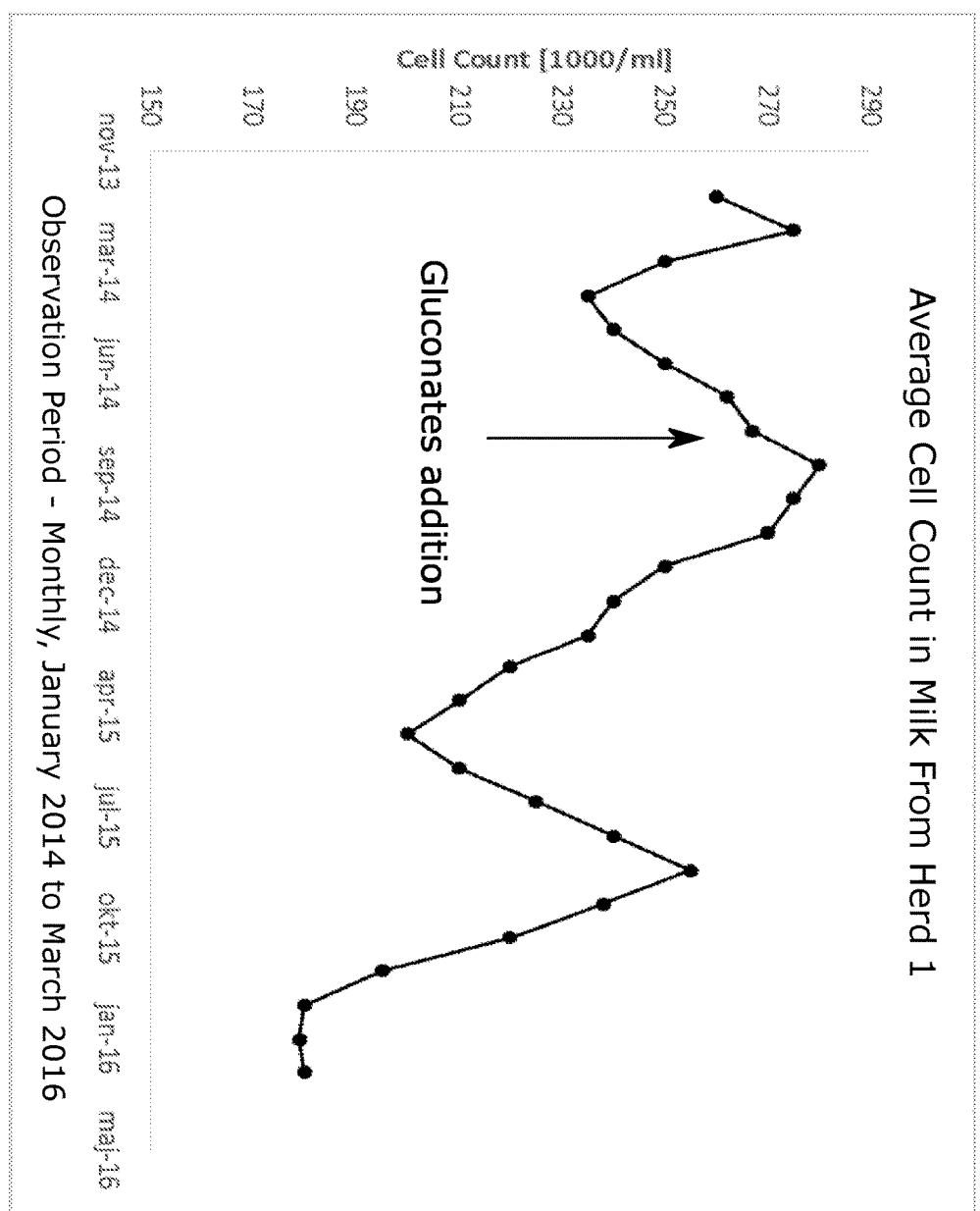
FIG. 4: Average cell count in milk from a cowherd allowed to graze.

Herd 1 represent a particular situation in that this herd was the only herd to graze. In the grazing season (May 1st to Sep. 1st), the bacterial levels in the grazing cows' milk increase for this reason alone, significantly beyond the effect of any bacterial infections. FIG. 4 details an expanded timeline comprising the data from FIG. 1 and earlier and further comprising the observation period for the second study.

As can be gathered from the data in FIG. 4, the average maximum observed infection level is reduced by about 25.000 cells/ml as an effect of the changed diet, and the average minimum obtainable infection level during indoors stall conditions is also reduced, but significantly stronger, by about 60.000 cells/ml, from about 240 k cells/ml at grazing start in May 2014 down to about 180 k cells/ml about two months before grazing start in May 2016. Before the diet change, cell counts below 225 k cells/ml were not observed on average across the herd, whether in stall nor when grazing.

Again, this result is consistent with a general reduction in the bacterial infection level in reply to the concomitant treatment of digital dermatitis with salicylic acid bandages and the oral administration of zinc and copper in the form of zinc and copper gluconates added to the feed of the cattle.

CLOSING COMMENTS

Salicylic acid bandages are well-established means of curing digital dermatitis lesions in claw-bearing animals and in particular in cattle. However, the use of such bandages merely provides short term relief and do not contribute to a reduction of the general infection level in a herd where cross-infection is ubiquitous. Neither is it known for mineral feed comprising zinc and copper to be the cause of a general reduction of the bacterial infectious level, as measured from the total cell counts/ml in milk from lactating herd members, however, in the present situation concomitant treatment according to the above implemented method causes both healing in the herd of lesions as well as showing a strong and prolonged preventive and anti-bacterial effect. This synergistic result is to the best of the present inventor's knowledge, not hitherto reported.

In the present disclosure, it shall be understood that the term "comprising" as used in the claims does not exclude, where appropriate, other elements or steps, and that the term "a" or "an" as used in the claims does not exclude, where appropriate, a plurality.

Although the present invention has been described in detail for purpose of illustration, it is understood that such detail is solely for that purpose, and variations can be made therein by those skilled in the art without departing from the scope of the invention.

The invention claimed is:

1. A method of treating and preventing digital dermatitis in a claw-bearing animal, comprising supplying zinc gluconate and copper gluconate for oral use in to the feed of said animal in an effective amount of zinc and copper, feeding said animal with said feed for a time period of at least 3 weeks, and concomitantly treating any diagnosed digital dermatitis lesion in said animal with a standard care topical treatment until said lesion is healed, wherein said zinc gluconate is administered in an amount of between 35 to 500 mg zinc per kg dry feed and said copper gluconate is administered in an amount of between 5 and 40 mg copper per kg dry feed.

2. A method according to claim 1, wherein said animal is a domesticated claw-bearing animal.

3. A method according to claim 1, wherein said animal is a bovine and said digital dermatitis is bovine digital dermatitis.

4. A method according to claim 1, wherein said standard care topical treatment comprises topically treating said lesion with an antibacterial agent and/or an antifungal agent.

5. A method according to claim 4, wherein said standard care topical treatment comprises topically treating said lesion with a bandage comprising an antibacterial agent and/or an antifungal agent.

6. A method according to claim 4, wherein said antibacterial agent is salicylic acid.

7. A method according to claim 1, wherein said zinc gluconate and/or copper gluconate is mixed with silage.

8. A method according to claim 1, wherein said zinc gluconate and/or copper gluconate is mixed to a concentrates feed.

9. A method of treating and preventing digital dermatitis in a herd of claw-bearing animals, said method comprising supplying zinc gluconate and copper gluconate for oral use in an effective amount with the feed to said herd while concomitantly treating any diagnosed digital dermatitis lesion of an animal in said herd of animals according to the method of claim 1, followed by continuing for at least 3 months supplying zinc gluconate and copper gluconate for oral use in said effective amount in the feed to said herd and concomitantly treating any diagnosed lesion of any animal in said herd of animals.

10. Silage or concentrates feed, respectively comprising zinc gluconate between 35 to 500 mg zinc per kg dry silage or concentrates feed, and copper gluconate between 5 and 40 mg copper per kg dry silage or concentrates feed, for use in a method according to claim 1.

* * * * *